United States Patent [19]

Geria

[11] 4,229,432

[45] Oct. 21, 1980

[54] ANTIPERSPIRANT STICK COMPOSITION

[75] Inventor: Navin Geria, Elizabeth, N.J.

[73] Assignee: Bristol-Myers Company, New York, N.Y.

[21] Appl. No.: 897,888

[22] Filed: Apr. 19, 1978

[51] Int. Cl.[3] .......................... A61K 7/34; A61K 7/38

[52] U.S. Cl. .............................. 424/68; 424/DIG. 5; 424/66

[58] Field of Search .......................... 424/DIG. 5, 68

[56] References Cited

U.S. PATENT DOCUMENTS

| | | | |
|---|---|---|---|
| 2,819,995 | 1/1958 | Wassell | 424/DIG. 5 |
| 2,892,732 | 6/1959 | Rockland | 424/DIG. 5 |
| 3,211,618 | 10/1965 | Kambersky | 424/DIG. 5 |
| 3,255,082 | 6/1966 | Barton | 424/DIG. 5 |
| 3,792,068 | 2/1974 | Luedders et al. | 424/47 |
| 3,856,931 | 12/1974 | Fuchs et al. | 424/DIG. 5 |
| 4,049,792 | 9/1977 | Elsnau | 424/66 |
| 4,083,956 | 4/1978 | Shelton | 424/68 |

FOREIGN PATENT DOCUMENTS

| | | | |
|---|---|---|---|
| 958338 | 11/1974 | Canada | 424/47 |

*Primary Examiner*—Dale R. Ore

*Attorney, Agent, or Firm*—Irving Holtzman; George A. Mentis

[57] ABSTRACT

An antiperspirant stick composition in which the antiperspirant material is maintained substantially homogeneously distributed throughout the stick by virtue of the presence of certain waxy materials.

9 Claims, No Drawings

ANTIPERSPIRANT STICK COMPOSITION

BACKGROUND OF INVENTION

This invention relates to an antiperspirant composition in the form of a stick. More particularly, it concerns an antiperspirant composition in the form of a stick in which the antiperspirant material is distributed substantially homogeneously throughout the stick.

It is well known in the prior art to prepare stick antiperspirant compositions. These, in general, are prepared by forming a liquid melt of a waxy base, incorporating the antiperspirant material e.g. aluminum chlorhydroxide in the liquid melt, pouring the liquid melt containing the antiperspirant material into a mold and allowing the melt to cool and solidify. Processes of this character are described in U.S. Pat. No. 4,049,792 and "Cosmetics Science and Technology" edited by Edward Sagarin, Interscience Publishers, Inc. New York, 1957 p. 730.

It has been found, however, that when these sticks are prepared in accordance with the prior art methods, the antiperspirant material was not uniformly distributed throughout the stick. The antiperspirant material tended to settle towards the bottom of the stick, so that the concentration of the antiperspirant material in the upper ¼ of the stick was significantly less than that found in the rest of the stick. This is obviously a disadvantage since during the early use of the stick, insufficient active material may be delivered per application; whereas, in the later use of the stick more active material may be deposited than is required.

SUMMARY OF INVENTION

It has now been found that the above noted disadvantages in the prior art products may be avoided by employing in the waxy base certain particular waxy materials defined in more detail below that appear to have gelling properties. These will ordinarily constitute between about 0.50% to about 10.00% by weight of the stick composition and preferably about 2% by weight.

DESCRIPTION OF INVENTION

The antiperspirant sticks of the present invention will generally comprise as principal components a low melting wax which will serve as the backbone for the antiperspirant stick and an emollient which will give the stick the requisite organoleptic properties. In addition, it will contain the active antiperspirant material and preferably also a surfactant. Optionally, it will also contain a tinting agent, an antioxidant and a fragrance. As an essential component, it will contain certain waxy materials defined in more detail below which, it is believed, function as gelling agents.

Although Applicant does not want to be bound by any theory, it is believed that the effectiveness of certain waxy materials, hereinafter for convenience referred to as "waxy gelling agents" in maintaining the antiperspirant homogeneously distributed in the stick is due to the gelling action of these waxy materials. It is believed that after the waxy melt containing the antiperspirant material and the waxy gelling agent are poured into the mold, the material begins to cool and the antiperspirant material tends to settle towards the bottom of the cooling waxy mass. However, it is thought that the gellation of the cooling waxy mass brought about by the "waxy gelling agents" traps the antiperspirant material in the gel structure and prevents it from settling towards the bottom of the stick.

The "waxy gelling agents" that may be employed in the present invention can be any of the waxes described below:

FT-300 Wax: As used herein, this refers to a wax of the Veba-Waxes Series "FT" marketed by Dura Commodities. It is a saturated, synthetic hard paraffin of formula $CH_3(CH_2)_nCH_3$ and is chemically neutral, colorless and high melting. It is free from aromatic and unsaturated compounds and contains neither sulfur nor any halogens. Its structure is characterized as fine crystalline; its appearance in the solid state is white and opaque. It forms a clear solution in the common wax solvents at elevated temperatures; at room temperature it is practically insoluble and has the following properties:

| Property | Value |
|---|---|
| Molecular wt., osmometric, approx. | 730 |
| Congealing Point, °C. ASTM D-938 | 96–98 |
| Drop Point, °C., ASTM D-127 | 107–111 |
| Penetration 25° C., ASTM D-1321 | 1 |
| Ball Pressure Hardness kg/cm² DIN 51 579 | 355/344 |
| Kinetic Viscosity, cstks, 120° C. (Vogel-Ossag) | 12 |
| Iodine No. | 0.1 |
| Acid Value, Saponification Value | nil |
| Color | white |
| Form | flakes |

This wax conforms to paragraph 121.2575 "Paraffin Synthetic" of the code of U.S. Federal Regulation to food and drug additives and is listed in the CTFA Dictionary page 321/322.

Paraffin Wax 133°/135° F.: As used herein, this refers to a fully refined paraffin wax marketed by Frank B. Ross and Co., Inc. having a melting in the range of from about 133°/135° F. This has a viscosity of 39 at 210° F., an oil content of 0.2–0.5% by weight, a penetration value of 12 at 77° F., a Flash Point of 430° F., a density of 6.48 lbs/gallon and a Saybolt color of 30.

195 White Wax: As used herein, this refers to white paraffin wax marketed by the Petrolite Company having a melting point of 195.5° F. and also known as "Be Square 195". This consists of n-paraffine, branched chain paraffinic and napthenic hydrocarbon in the C-36 to C-60 range. The physical properties of this wax are set out below:

| Property | Test Method | Units |
|---|---|---|
| Melting Point | ASTM D-127 | °F. (°C.) 195.5 (90.8) |
| Congealing Point | ASTM D-938 | °F. (°C.) 184 (84.4) |
| Density at 75° F. (23.9° C.) | ASTM D-1168 | grams/cc 0.9344 |
| Density at 210° F. (98.8° C.) | ASTM D-1168 | grams/cc 0.7459 |
| Viscosity at 210° F. (98.8° C.) | ASTM D-88 | SUS 77.5 |
| Viscosity at 210° F. (98.8° C.) | ASTM D-445 | c Sts. 14.9 |
| Penetration at 77° F. (25° C.) | ASTM D-1321 | 0.1 mm 6.5 |
| Penetration at 130° F. (54.4° C.) | ASTM D-1321 | 0.1 mm 26. |
| Color | ASTM D-1500 | 0.5– |

Victory White Wax: As used herein, this refers to a paraffin wax marketed by the Petrolite Company. It is a petroleum derived microcrystalline wax containing relative high concentrations of branched and naphthenic hydrocarbon and relatively low concentrations of n-paraffinic hydrocarbon (20–40%) and has the following properties:

| Property | Test Method | Units |
|---|---|---|
| Melting Point | ASTM D-127 | °F. (°C.) 175 (79.4) |
| Congealing Point | ASTM D-938 | °F. (°C.) 164 (73.3) |
| Density at 75° F. (23.9° C.) | ASTM D-1168 | grams/cc 0.9254 |
| Density at 210° F. (98.8° C.) | ASTM D-1168 | grams/cc 0.7668 |
| Viscosity at 210° F. (98.8° C.) | ASTM D-88 | SUS 85. |
| Viscosity at 210° F. (98.8° C.) | ASTM D-445 | c Sts. 16.7 |
| Penetration at 77° F. (25° C.) | ASTM D-1321 | 0.1 mm 29 |
| Penetration at 210° F. (43.3° C.) | ASTM D-1321 | 0.1 mm 144 |
| Color | ASTM D-1500 | 1.0– |
| Flash Point | ASTM D-92 | °F. (°C.) 560. (292.3) |

Multiwax 180-M: As used herein, this refers to a microcrystalline wax marketed by the Witco Chemical Company. Chemically, it is mixture of alkylated naphthenes (saturated cycloparaffins), isoparaffins (branched chains) with varying amounts of normal paraffins (straight chains). It has an average molecular weight of 580 to 900 with individual molecules containing from 30 to 60 carbon atoms. The physical properties of this wax are as follows:

| Melting Point (ASTM D-127) | Needle Penetration at 77° F. (ASTM D-1321) | Saybolt Viscosity at 210° F., SUS (ASTM D-88) | Color Visual | ASTM D-1500 | Flash Point ASTM D92 |
|---|---|---|---|---|---|
| 180/190 | 15/20 | 75/90 | light yellow | 1.0/2.0 | 530 Min. |

The quantity of "waxy gelling agent" that may be contained in the stick compositions of this invention may vary somewhat. However, as indicated above, it generally will fall in the range of from about 0.50% to 10.0% by weight based on the total weight of the composition and will preferably be about 2% by weight.

The backbone of the antiperspirant sticks of the present invention will generally comprise a low melting point waxy material that is a waxy material having a melting point of from about 100° F. to 150° F. Typical suitable low melting point waxes are fatty acids containing from about 8 to about 22 carbon atoms, fatty alcohols containing from about 8 to about 22 carbon atoms, silicone waxes and glycerol monostearate. Especially useful materials of this type are the $C_8$ to $C_{22}$ fatty acids and $C_8$ and $C_{22}$ fatty alcohols. By way of example, the following may be mentioned: cetyl alcohol, stearyl alcohol, myristyl alcohol, Lauryl alcohol and Behenyl alcohol. However, the preferred low melting point wax is stearyl alcohol.

The quantity of low melting point wax that may be contained in the present antiperspirant stick compositions may also vary somewhat. Ordinarily, this will comprise about 16.0% to about 35.0% by weight based on the total weight of the composition and preferably about 27% by weight.

Another major component of the antiperspirant stick compositions of this invention is the emollient. This is selected for its organoleptic characteristics and its ease of removal with a surfactant such as soap. Typical emollients that are useful for the present purposes include non-polar liquids which will ordinarily take the form of a non-volatile oil. Suitable non-volatile oils for this purpose are organic oily liquids which are non-polar in character and have (a) boiling point under atmospheric pressure not lower than about 120° C.; (b) a specific gravity between about 0.7 and 1.6, preferably between 0.7 and 1.2. These include such materials as liquid hydrocarbon (mineral oil); fatty acid esters (isopropyl myristate, isopropyl palmitate); branched chain fatty acid esters (2-ethyl hexyl palmitate) diesters of dicarboxylic acids (diisopropyl adipate); polyoxy alkylene glycol esters (polypropylene glycol 2000 monooleate); propylene glycol diesters of short chain fatty acids (C8–C10) (Neobee M-20); polyoxyethylene esters (polyoxyethlene (4) lauryl ether (Brij 30), polyoxyethylene fatty acids, polyoxypropylene cetyl ether (procetyl); higher fatty alcohols (oleyl, hexadecyl, lauryl); Silicone Oils (dimethyl polysiloxane, 10-1000 centistokes); Volatile Silicones (e.g. Cyclomethicone 251). Mixtures of the about non-polar liquids are equally suitable for the purpose of this invention. The emollient preferred for use in the present invention is 2-ethylhexyl palmitate. This may be described by formula

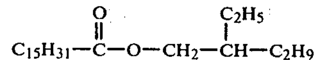

The quantity of emollient that will be contained in the antiperspirant stick composition of this invention may also vary somewhat. As a general rule, it will comprise from about 20.0% to about 60.0% by weight of the stick composition and preferably about 47% by weight.

The principal active ingredient in the antiperspirant stick composition of this invention is of course the antiperspirant material. This will ordinarily take the form of an astringent aluminum or zirconium compound or mixtures thereof; that is, mixtures of aluminum compounds or mixtures of zirconium compounds or mixtures of aluminum compounds with zirconium compounds. Usually, the aluminum or zirconium compounds will take the form of astringent salts. Typical antiperspirant actives include impalpable aluminum chlorhydroxide and aluminum hydroxybromide, aluminum chloride as well as the antiperspirant actives disclosed in U.S. Pat. No. 3,792,068 issued Feb. 12, 1974 to Luedders et al.

This Luedders et al patent discloses a complex of aluminum, zirconium and amino acid by:

A. Co-dissolving in water (1) one part $Al_2(OH)_{6-m}X_m$, wherein X is an anion selected from the group consisting of chloride, bromide and iodide and m is a number from about 0.8 to about 1.2;

(2) n parts ZrY wherein Y is an anion selected from the group consisting of —O(OH)Cl and $OCl_2$, and where n has a value of from about 0.16 to about 1.2;

(3) p parts neutral amino acid selected from the group consisting of glycine, dl-tryptophane, dl-beta-phenylalanine, dl-valine, dl-methionine and beta-alanine, and where p has a value of from about 0.06 to about 0.53;

B. Co-drying the resultant mixture at a temperature of from about 100° C. to about 230° C. to a moisture level of from about 0.5% to about 15% by weight; and C. Comminuting the resultant dried inorganic-organic antiperspirant complex into the form of an impalpable powder.

The preferred aluminum compound for preparation of the Luedders et al complex is aluminum chlorhydroxide of the formula $Al_2(OH)_5Cl2H_2O$. The preferred zirconium compound for preparation of the Leudders et al complex is zirconyl hydroxy-chloride having the formula $ZrO(OH)Cl3H_2O$. The preferred amino acid for preparing the Luedders et al complex is glycine of the formula $CH_2(NH_2)COOH$. Salts of such amino acids can also be employed in such antiperspirant complexes.

Other suitable actives for use in the present invention comprise mixtures of aluminum chloride with other aluminum salts less acidic than aluminum chloride e.g. aluminum hydroxy-chloride (or aluminum chlorhydroxide). These are described in Canadian Pat. No. 958,338 issued Nov. 26, 1974.

As will be noted this patent discloses an aluminum antiperspirant material comprising a mixture of aluminum chloride powder and a powdered water soluble salt of aluminum which is less acidic than aluminum chloride. The quantities of aluminum chloride and said water soluble aluminum salt which may comprise the aluminum antiperspirant material may vary somewhat. However, in terms of percentages by weight of the total of powdered aluminum antiperspirant material, the aluminum chloride will generally constitute 10 to 50% and preferably 15 to 20%, the balance being made up by said less acidic aluminum salt. In the case of aluminum chlorhydroxide, it is convenient to express the relative amounts of aluminum chloride and aluminum chlorhydroxide in terms of the molar ratios of aluminum to chloride in the dry mixture. In this case, the molar ratio of aluminum to chloride will be in the range of from about 0.78:1 to 1.95:1. Preferably, this ratio will be in the range of from 1.33:1 to In preparing this antiperspirant powder mix in addition to the aluminum chloride any of the other water soluble aluminum compounds (less acidic than aluminum chloride) known in the prior art as effective as antiperspirant materials may be employed. By way of illustration of these, mention may be made of aluminum chlorhydroxide, aluminum sulfate, "rehydrol" (aluminum chlorhydroxide-propylene glycol complex), complex of zinc phenolsulfonate and chlorhydrol (ratio of aluminum to zinc from 12:1 to 6:1), aluminum potassium sulfate, "Wickenol 363D" (aluminum chlorhydroxide-polyethylene glycol mixture), etc. However, the preferred aluminum compound of this character is aluminum chlorohydrate. In the preferred form, it is employed as an ultrafine powder.

The quantity of antiperspirant material that will be contained in the sticks of the present invention may vary somewhat. Ordinarily, it will constitute between about from about 10.0% to about 50% by weight based on the total weight of the composition and preferably about 22.00% by weight.

It is also advantageous to incorporate a surfactant in the antiperspirant stick composition of this invention. This facilitates better contact between the antiperspirant material and the skin and helps to increase its activity. Moreover, it also facilitates the removal of the product while washing or bathing. A number of surfactants are known in the prior art which are suitable for the present purposes. By way of example, mention may be made of the following: Sorbitan fatty esters (Arlacel 20), Polyoxyethylene sorbitol lanolin derivatives (Atlas G-1471), Polyoxyethylene lanolin derivative (Atlas G-1795), Polyoxyethylene fatty ethers (Brij 35), Polyoxyethylene 25 propylene glycol stearate (G-2162), Polyoxyethylene stearate (Myrj 59), Polyoxyethylene sorbitan fatty ethers (Tween 20), Polyoxypropylene polyoxyethylene condensate (Pluronic F-127).

One surfactant that is especially useful for the purposes of the present invention is PEG-25-Propylene Glycol Stearate. This has the formula:

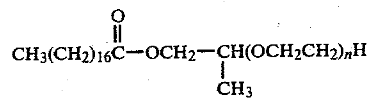

where n has an average value of 25.

The quantity of surfactant that will be contained in the present composition may vary over a range. Generally, it will contain from about 0.50% to about 10.0% by weight based on the total weight of the composition and preferably about 2.0% by weight.

Tinting agents (e.g. Titanium dioxide), antioxidants (e.g. butylated hydroxytoluene) and perfume may be added to the present antiperspirant stick compositions as optional features. These will usually be added to make a more commercially acceptable product.

The antiperspirant stick compositions of this invention may be made a variety of ways known to those skilled in the art. In one procedure, the emollient is first blended with the tinting agent e.g. titanium dioxide (Step 1). The antiperspirant, preferably in the form of a fine powder, is then mixed with the material made in Step 1 using light agitation and the temperature of this mixture is raised (Step 2). The waxy gelling agent, low melting point wax, surfactant and antioxidant are mixed together and heated to form a clear melt (Step 3). The contents of Step 2 and Step 3 are mixed together to form a homogeneous suspension which is used to fill the stick molds.

The following Examples are given to further illustrate the present invention. It is to be understood, however, that the invention is not limited thereto.

EXAMPLE 1

| Formula 1349 | % by Wt. |
|---|---|
| 2-Ethylhexyl Palmitate | 45.72 |
| Titanium Dioxide | 0.23 |
| Stearyl Alcohol | 27.00 |
| FT-300 Wax | 2.00 |
| PEG (25) Propylene Glycol Stearate | 2.00 |
| Butylated Hydroxytoluene | 0.05 |
| Aluminum Chlorohydrate Ultrafine Powder | 22.00 |
| Perfume | 1.00 |
| | 100.00 |

1. Combine 2-ethylhexyl palmitate with titanium dioxide and mix in a Waring blender at medium speed for 5 minutes.

2. Transfer the mixture from step 1 into a suitable stainless steel steam-jacketed kettle and add aluminum chlorohydrate ultrafine powder using moderate lightning' mixer agitation. Slowly raise the temperature of this mixture to 110° F. under moderate agitation.

3. In another stainless steel steam-jacketed kettle, combine the FT-300 wax, stearyl alcohol, PEG (25) propylene glycol stearate and butylated hydroxytoluene. Melt until clear by heating to 210° F.

4. Add the contents of step 2 at 110° F. to step 3 at 185° F. under moderate agitation. A uniform homogeneous suspension results. Cool the batch to 125° F.

5. Add the perfume at 125° F. just before filling into containers.

6. Product Filling Instructions:

A. Filling temperature: 125°±2° F.

B. Cooling temperature: 15 minutes at 40° F.

C. Insert a tubular hollow probe through the center of the stick over the threaded shaft to a depth of approximately ¾" prior to flaming to eliminate voids.

D. The sticks are individually flamed under a 250 watt infrared lamp for one minute (sticks are approximately 2-3" from the lamp).

EXAMPLE 2

| Formula 1353 | % by Wt. |
|---|---|
| 2-Ethylhexyl Palmitate | 46.52 |
| Titanium Dioxide | 0.23 |
| Stearyl Alcohol | 27.00 |
| FT-300 Wax | 2.00 |
| PEG (25) Propylene Glycol Stearate | 2.00 |
| Butylated hydroxytoluene | 0.05 |
| Aluminum Chlorohydrate Ultrafine Powder | 22.00 |
| Perfume | 0.20 |
| | 100.00 |

1. Combine 2-ethylhexyl palmitate with titanium dioxide and mix in a Waring blender at medium speed for 5 minutes.

2. Transfer the mixture from step 1 into a suitable stainless steel steam-jacketed kettle and add aluminum chlorohydrate ultrafine powder using moderate lightnin' mixer agitation. Slowly raise the temperature of this mixture to 110° F. under moderate agitation.

3. In another stainless steel steam-jacketed kettle, combine the FT-300 wax, stearyl alcohol, PEG (25) propylene glycol stearate and butylated hydroxytoluene. Melt until clear by heating to 210° F.

4. Add the contents of step 2 at 110° F. to step 3 at 185° F. under moderate agitation. A uniform homogeneous suspension results. Cool the batch to 125° F.

5. Add the perfume at 125° F. just before filling into containers.

6. Product Filling Instructions:

A. Filling temperature: 125°±2° F.

B. Cooling temperature: 15 minutes at 40° F.

C. Insert a tubular hollow probe through the center of the stick over the threaded shaft to a depth of approximately ¾" prior to flaming to eliminate voids.

D. The sticks are individually flamed under a 250 watt infrared lamp for one minute (sticks are approximately 2-3" from the lamp).

EXAMPLE 3

| Formula 1290-8 | % by Wt. |
|---|---|
| 2-Ethylhexyl Palmitate | 47.72 |
| Titanium Dioxide | 0.23 |
| Stearyl Alcohol | 20.00 |
| FT-300 Wax | 4.00 |
| PEG (25) Propylene Glycol Stearate | 5.00 |
| Butylated Hydroxytoluene | 0.05 |
| Aluminum Sesquichlorohydrate Glycine mixture, Impalpable Powder | 22.00 |
| Perfume | 1.00 |
| | 100.00 |

EXAMPLE 4

| Formula 1290-18 | % by Wt. |
|---|---|
| 2-Ethylhexyl Palmitate | 47.72 |
| Titanium Dioxide | 0.23 |
| Stearyl Alcohol | 25.00 |
| FT-300 Wax | 2.00 |
| PEG (25) Propylene Glycol Stearate | 2.00 |
| Butylated Hydroxytoluene | 0.05 |
| Aluminum Sesquichlorohydrate Impalpable Powder | 22.00 |
| Perfume | 1.00 |
| | 100.00 |

EXAMPLE 5

| Formula 1290-27 | % by Wt. |
|---|---|
| 2-Ethylhexyl Palmitate | 47.72 |
| Titanium Dioxide | 0.23 |
| Stearyl Alcohol | 25.00 |
| FT-300 Wax | 2.00 |
| PEG (25) Propylene Glycol Stearate | 2.00 |
| Butylated Hydroxytoluene | 0.05 |
| Aluminum Zirconium Pentachlorohydrate ($Al/_{Zr} = 6/1$) Impalpable Powder | 22.00 |
| Perfume | 1.00 |
| | 100.00 |

EXAMPLE 6

| Formula 1290-79 | % by Wt. |
|---|---|
| 2-Ethylhexyl Palmitate | 49.72 |
| Titanium Dioxide | 0.23 |
| Behenyl Alcohol | 23.00 |
| FT-300 Wax | 2.00 |
| PEG (25) Propylene Glycol Stearate | 2.00 |
| Butylated Hydroxytoluene | 0.05 |
| Aluminum Dichlorohydrate Impalpable Powder | 22.00 |
| Perfume | 1.00 |
| | 100.00 |

To test the distribution of the aluminum chlorohydrate in the finished antiperspirant stick made in accordance with Examples 1 and 2, the top ¼" of sample sticks was cut off and assayed for aluminum chlorohydrate. Similarly, the middle portion of each stick (1½ inches down) was assayed. The results of these tests are summarized in Table I below:

TABLE I

| Sample | Theoretical % by Wt. Aluminum Chlorohydrate | Found % by Wt. | |
|---|---|---|---|
| | | Top ¼" | Middle 1½" |
| Formula 1349 | 22 ± 1.5 | 22.3 ; 22.0 | 22.3 ; 23.0 |
| Formula 1352 | 22 ± 1.5 | 19.8 ; 19.6 | 23.2 ; 22.8 |

To compare the effect of the variation of the "gelling wax" in the same formula on the distribution of aluminum chlorohydrate in various sticks an aluminum chlorohydrate assay was carried on the top ¼" of some sticks and on the top ¼" and middle 1½" of other sticks. The formulas of the sticks tested are given in Table II. The assay for each of these formulas is given in Table III.

TABLE II

| Ingredients | % by Weight | | | | | | | | |
|---|---|---|---|---|---|---|---|---|---|
| | 1350 5A | 1350 6A | 1350 6B | 1350 6C | 1350 6D | 1350 6E | 1350 11 | 1290 83A | 1290 83B |
| 2-ethylhexyl palmitate | 45.72 | → | → | → | → | → | → | → | → |
| Titanium dioxide | 0.23 | → | → | → | → | → | → | → | → |
| Stearyl alcohol | 27.0 | → | → | → | → | → | → | → | → |
| PEG (25) propylene glycol stearate | 2.0 | → | → | → | → | → | → | → | → |
| Butylated hydroxytoluene | 0.05 | → | → | → | → | → | → | → | → |
| Aluminum Chlorohydrate (powder) | 22.0 | → | → | → | → | → | → | → | → |
| Perfume | 1.0 | → | → | → | → | → | → | → | → |
| Paraffin Wax 128°/130° F. | — | — | — | — | — | — | 2.0 | — | — |
| 195 White Wax | — | — | 2.0 | — | — | — | — | — | — |
| Victory White Wax | — | — | — | — | — | 2.0 | — | — | — |
| Multiwax 180-M | — | — | — | 2.0 | — | — | — | — | — |
| Paraffin Wax M.P. 143°/145° F. | — | — | — | — | — | — | — | — | 2.0 |
| Paraffin Wax M.P. 155°/160° F. | 2.0 | — | — | — | — | — | — | — | — |
| Multiwax 445 M.P. 170° F. | — | 2.0 | — | — | — | — | — | — | — |
| Multiwax 145A M.P. 145° F. | — | — | — | — | 2.0 | — | — | — | — |
| Paraffin Wax 133°/135° F. | — | — | — | — | — | — | — | 2.0 | — |

TABLE III

| Sample | Assay for Aluminum Chlorohydrate: Theoretical % w/w Aluminum Chlorohydrate | Found % w/w Aluminum Chlorohydrate |
|---|---|---|
| a. 1350-5A | | |
| 1. top ¼ inch | 22 ± 1.5 | 9.6, 9.6[3] |
| 2. middle (1 ½ down) | " | 28.5, 28.5 |
| b. 1350-6A | | |
| 1. Top¼ inch | " | 17.8, 17.8[3] |
| 2. middle (1½" down) | " | 23.1, 23.1 |
| *c. 1350-6B | | |
| 1. top ¼ inch | " | 20.7, 21.0[3] |
| 2. middle (1½" down) | " | 20.7, 20.5 |
| *d. 1350-6C | | |
| 1. top ¼ inch | " | 18.4, 18.3[3] |
| 2. middle (1½" down) | " | 21.2, 20.9 |
| e. 1350-6D | | |
| 1. top ¼ inch | " | 13.0, 13.0[3] |
| 2. middle (1½" down) | " | 20.5, 20.4 |
| *f. 1350-6E | | |
| 1. top ¼ inch | " | 19.0, 18.6[3] |
| 2. middle (1½" down) | " | 24.2, 24.0 |
| g. 1350-11 | | |
| 1. top ¼ inch | " | 9.34, 9.3[3] |
| 2. middle (1½" down) | " | 21.4, 21.2 |
| *h. 1290-83A | " | 21.9, 21.7[1] |
| | | 21.6, 21.2[2] |
| i. 1290-83B | " | 6.1, 5.5 6.1 |

TABLE III-continued

| Sample | Assay for Aluminum Chlorohydrate: Theoretical % w/w Aluminum Chlorohydrate | Found % w/w Aluminum Chlorohydrate |
|---|---|---|
| | | 8.1, 8.3[2] |

[1]Original assay on composite of 3 sticks, top ¼"
[2]Assay performed on second set of 2 sticks, top ¼"
[3]Analysis run on the stick composite
*Products representative of the present invention Any assay for aluminum chlorohydrate of the top ¼" of a stick that is below 18% is taken to be unsatisfactory. This would be greater than 4% below the theoretical which is 22%. Samples (a), (b), (e), (g) and (i) are therefore unsatisfactory by this criteria.

It will be seen from Table III that the use of seemingly closely related waxes give dramatically different results. Thus, by using Paraffin Wax MP 143°/145° F. (1350-5A) the aluminum chlorohydrate assay for the top ¼" was as little as 9.6% (i.e. about 12.4% below the theoretical) and with Paraffin Wax 128°/130° F. (1350-11), the assay of the top ¼" was on the average of about 7% (i.e. 15% below the theoretical). In contrast to this, with Paraffin Wax 133°/135° F. (1290-83A), the top ¼" assayed on the average of about 21.6 that is only about 0.4% below the theoretical.

What is claimed is:

1. In an antiperspirant stick composition consisting essentially of, based on the total weight of the composition:

(a) from about 16% to about 35% by weight of a low melting wax selected from the group consisting of a fatty acid containing from about 8 to 22 carbon atoms, a fatty alcohol containing from about 8 to about 22 carbon atoms, a silicone wax and glycerol monostearate;

(b) from about 20% to 60% of an emollient; and (c) from about 10% to 50% of an antiperspirant material; the improvement which comprises:

(d) from about 0.5% to about 10.0% of the additional waxy agent FT-300 Wax incorporated in said stick composition, said FT-300 Wax being characterized in that it is a saturated, synthetic hard paraffin of formula $CH_3(CH_2)_nCH_3$ and is chemically neutral, colorless and high melting; is free from aromatic and unsaturated compounds and contains neither sulfur nor any halogens; has a structure that is characterized as fine crystalline; appearance in the solid state is white and opaque; and forms a clear solution in the common wax solvents at elevated temperature it is practically insoluble and has the following properties:

| | |
|---|---|
| Molecular weight, osmometric approx. | 730 |
| Congealing point, (°C. ASTM) (D-938) | 96-98 |
| Drop Point (°C., ASTM D-127) | 107-111 |
| Penetration (25° C., ASTM D-1321) | 1 |
| Ball Pressure Hardness kg/cm$^2$ DIN 51 579 | 355/344 |
| Kinetic Viscosity, cstks, 120° C. (Vogel-Ossag) | 12 |
| Iodine No. | 0.1 |
| Acid Value, Saponification Value | nil |
| Color | white |
| Form | flakes |

said FT-300 Wax serving to prevent the settling of said antiperspirant material.

2. A composition according to claim 1 including a surfactant.

3. A stick composition according to claim 2 including a material selected from the group consisting of a tinting agent, an antioxidant and a perfume.

4. A composition according to claim 1 in which said antiperspirant material is selected from the group consisting of an astringent aluminum salt, an astringent zirconium salt and mixtures thereof.

5. A composition according to claim 4 in which said antiperspirant material is aluminum chlorohydrate.

6. A composition according to claim 4 wherein said antiperspirant material is a mixture of aluminum chloride and aluminum chlorohydrate.

7. A composition according to claim 4 in which the emollient is 2-ethylhexyl palmitate.

8. A composition according to claim 4 in which said low melting wax is stearyl alcohol.

9. A composition according to claim 4 in which said surfactant is PEG (25) propylene glycol stearate.

* * * * *

UNITED STATES PATENT AND TRADEMARK OFFICE
CERTIFICATE OF CORRECTION

PATENT NO. : 4,229,432

DATED : October 21, 1980

INVENTOR(S) : Navin Geria

It is certified that error appears in the above-identified patent and that said Letters Patent are hereby corrected as shown below:

Column 5, line 38, after "to" insert -- 1.79:1 --

Signed and Sealed this

*Seventeenth* Day of *February 1981*

[SEAL]

*Attest:*

RENE D. TEGTMEYER

*Attesting Officer* *Acting Commissioner of Patents and Trademarks*